(12) United States Patent
Hohlbein et al.

(10) Patent No.: US 8,714,353 B2
(45) Date of Patent: May 6, 2014

(54) PACKAGE OF ORAL CARE IMPLEMENTS AND METHOD OF USING THE SAME

(75) Inventors: Douglas Hohlbein, Hopewell, NJ (US);
Alan Sorrentino, Cranbury, NJ (US);
James Kemp, Basking Ridge, NJ (US);
Emily Fink, New York, NY (US); David Lee, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/997,332

(22) PCT Filed: Dec. 22, 2010

(86) PCT No.: PCT/US2010/061878
§ 371 (c)(1),
(2), (4) Date: Jun. 24, 2013

(87) PCT Pub. No.: WO2012/087316
PCT Pub. Date: Jun. 28, 2012

(65) Prior Publication Data
US 2013/0277254 A1  Oct. 24, 2013

(51) Int. Cl.
*B65D 83/10*  (2006.01)
(52) U.S. Cl.
USPC .......................................... 206/362; 220/524
(58) Field of Classification Search
USPC ............... 206/362, 362.1, 362.2, 362.3, 443; 220/524, 525, 553, 554, 555
See application file for complete search history.

(56) References Cited

U.S. PATENT DOCUMENTS

| | | | |
|---|---|---|---|
| 1,507,466 | A | 9/1924 | Collins |
| 1,621,514 | A | 3/1927 | Mann |
| 2,280,431 | A | 4/1942 | Hart |
| D154,689 | S | 8/1949 | Lundgren |
| 2,953,242 | A | 9/1960 | Shaw |
| 3,141,712 | A | 7/1964 | Holmes et al. |

(Continued)

FOREIGN PATENT DOCUMENTS

| | | |
|---|---|---|
| DE | 21 14 603 | 10/1972 |
| DE | 30 02 109 | 7/1981 |

(Continued)

OTHER PUBLICATIONS

International Search Report and the Written Opinion of the International Searching Authority issued in International Application PCT/US2010/061878 mailed Dec. 8, 2011.

(Continued)

*Primary Examiner* — Jacob K Ackun
(74) *Attorney, Agent, or Firm* — Ryan M. Flandro (57) ABSTRACT

A package (100) of articles, such as oral care implements (200) comprising: a tubular body (109) having a cavity (115), an open top end (167) and a closed bottom end (126). An annular wall (120) divides the cavity into a central cavity (125) and an annular cavity (115) that circumferentially surrounds the central cavity. A plurality of radial walls (130) extend from an outer surface (121) of the annular wall to an inner surface (112) of the tubular body and divide the annular cavity into a plurality of subcavities (135). At least one oral care implement is disposed within each of the subcavities. A cover (170) is coupled to at least one of the tubular body and the annular wall. The cover comprises a central opening (177) that forms a passageway into the central cavity and a dispensing opening (174).

22 Claims, 4 Drawing Sheets (56) References Cited

U.S. PATENT DOCUMENTS

| | | | |
|---|---|---|---|
| 3,482,728 A * | 12/1969 | Flax | 220/525 |
| 3,727,748 A | 4/1973 | Brown | |
| 3,744,672 A | 7/1973 | Dangles et al. | |
| 3,833,406 A | 9/1974 | White | |
| 3,881,868 A | 5/1975 | Duke | |
| 4,288,006 A | 9/1981 | Clover, Jr. | |
| 4,375,849 A | 3/1983 | Hanifl | |
| 4,522,315 A | 6/1985 | Rapp | |
| 4,583,661 A | 4/1986 | Clover, Jr. | |
| D292,528 S | 10/1987 | Weissenburger | |
| 4,915,219 A * | 4/1990 | Ottimo | 206/209.1 |
| 4,973,847 A | 11/1990 | Lackey et al. | |
| 4,995,511 A | 2/1991 | Evans | |
| 4,997,629 A | 3/1991 | Marchand et al. | |
| D319,875 S | 9/1991 | Lackey et al. | |
| D323,090 S | 1/1992 | Santarelli et al. | |
| D334,427 S | 3/1993 | Palazzolo et al. | |
| 5,245,117 A | 9/1993 | Withers et al. | |
| 5,277,312 A | 1/1994 | Vumbaca | |
| 5,522,497 A | 6/1996 | Stacy | |
| 5,566,823 A * | 10/1996 | Summers | 206/209.1 |
| 5,630,505 A | 5/1997 | Garcia | |
| 5,690,214 A * | 11/1997 | Gaines et al. | 206/209.1 |
| 5,762,199 A * | 6/1998 | Aguilera | 206/533 |
| 5,782,359 A * | 7/1998 | McAllister et al. | 206/538 |
| 5,873,462 A * | 2/1999 | Nguyen et al. | 206/366 |
| 5,938,058 A | 8/1999 | Kim | |
| 5,947,274 A | 9/1999 | Taskis et al. | |
| 5,967,315 A * | 10/1999 | Langtry, II | 206/315.11 |
| 6,135,279 A * | 10/2000 | Dryer | 206/362.1 |
| 6,176,384 B1 | 1/2001 | Voloshin | |
| 6,186,324 B1 | 2/2001 | Catterson | |
| 6,196,407 B1 * | 3/2001 | Liu | 220/263 |
| 6,387,068 B1 * | 5/2002 | Naughton | 604/2 |
| 6,935,515 B1 | 8/2005 | Sookoo | |
| 7,090,072 B1 * | 8/2006 | Elliott | 206/15.3 |
| 7,097,050 B1 | 8/2006 | McClellan et al. | |
| 7,125,187 B2 | 10/2006 | Osti | |
| 7,128,213 B2 * | 10/2006 | Tung et al. | 206/538 |
| 7,147,127 B2 | 12/2006 | Lepke et al. | |
| 7,213,603 B2 | 5/2007 | Pinsky | |
| 7,228,991 B2 | 6/2007 | Barraclough | |
| 2005/0073832 A1 | 4/2005 | Shilton et al. | |
| 2006/0000837 A1 | 1/2006 | Watson et al. | |
| 2007/0084735 A1 | 4/2007 | Lancesseur et al. | |
| 2007/0187271 A1 * | 8/2007 | Shaw | 206/362.3 |
| 2008/0012172 A1 | 1/2008 | Merical et al. | |
| 2009/0050500 A1 | 2/2009 | Ultimo | |
| 2009/0090723 A1 * | 4/2009 | Holbrook et al. | 220/521 |
| 2009/0200200 A1 | 8/2009 | Trappani et al. | |
| 2009/0307971 A1 | 12/2009 | Driscoll | |
| 2010/0300925 A1 | 12/2010 | Kan | |

FOREIGN PATENT DOCUMENTS

| | | |
|---|---|---|
| DE | 86 11 729 | 6/1986 |
| EP | 1 352 844 | 10/2003 |
| WO | WO 00/19880 | 4/2000 |
| WO | WO 2009/140627 | 11/2009 |

OTHER PUBLICATIONS

The Written Opinion of the International Preliminary Examining Authority issued in International Application PCT/US2010/061878 mailed Apr. 18, 2013.

* cited by examiner

PACKAGE OF ORAL CARE IMPLEMENTS AND METHOD OF USING THE SAME

CROSS-REFERENCE TO RELATED PATENT APPLICATIONS

The present application is a U.S. national stage application under 35 U.S.C. §371 of PCT Application No. PCT/US2010/061878, filed Dec. 22, 2010, the entirety of which is incorporated herein by reference.

FIELD OF THE INVENTION

The present invention relates generally to the field of packaging oral care implements, and specifically to a package of oral care implements having a moisture sensitive pre-applied oral care material.

BACKGROUND OF THE INVENTION

The advantages of good dental hygiene are well known. Often, however, oral care implements cannot be used due to a lack of a water source, such as when a user is driving in a vehicle or on-the-go. Oral care implements that can be used without a water source have recently been developed. For example, oral care implements have been developed that provide an oral care material within the oral care implement itself, such as through an integrated channel, for distribution through the oral care implement to the bristles. Disposable waterless oral care implements that utilize a pre-applied moisture sensitive capsule have also been introduced into the market.

Oral care implements, such as those described above, must be maintained in a sealed environment prior to use in order to prevent moisture from prematurely degrading and/or releasing the oral care material. As such, these oral care implements must be carefully packaged. Furthermore, users of disposable oral care implements need a place to dispose the oral care implements after use. Disposable oral care implements of the type discussed above are currently packaged in a plastic clamshell packages that are individually foil-sealed for protection. If a user uses a disposable oral care implement in a vehicle or another "on-the-go" location, the user must resort to either leaving the used disposable oral care implement loose within the vehicle or holding onto it until a proper waste basket can be located.

Hence, there is a need for a package that can contain oral care implements in a moisture-free environment prior to use. Furthermore, there is a need for a package that can contain a plurality of oral care implements such that one of the oral care implements can be removed from the package for use while the remainder of the oral care implements remain in moisture protected environment.

A need also exists for a package that can fit within a vehicle cup holder. Additionally, a need exists for a package that has a built-in "waste basket" compartment for disposal of the oral care implements after use.

BRIEF SUMMARY OF THE INVENTION

The present invention is directed to a package of oral care implements. The package has a central cavity and an annular cavity that circumferentially surrounds the central cavity. The annular cavity is divided into a plurality of subcavities. The package also has a rotatable cover that seals the subcavities from moisture in the external environment. The rotatable cover has a central opening that allows used oral care implements to be inserted into the central cavity for disposal and a dispensing opening through which unused oral care implements can be withdrawn from the subcavities In one embodiment, the invention can be a package of articles comprising: a tubular body having a cavity, an open top end and a closed bottom end; an annular wall disposed within the cavity, the annular wall dividing the cavity into a central cavity and an annular cavity, the annular cavity circumferentially surrounding the central cavity; a plurality of radial walls extending from an outer surface of the annular wall to an inner surface of the tubular body, the radial walls dividing the annular cavity into a plurality of subcavities; at least one article disposed within each of the subcavities; and an annular cover rotatably coupled to at least one of the tubular body and the annular wall so as to enclose a top end of the annular cavity, the annular cover comprising a central opening that forms a passageway into the central cavity from an external environment and a dispensing opening that forms a passageway into one of the subcavities from the external environment.

In one embodiment, the invention can be a package of oral care implements comprising: a tubular body having a cavity, an open top end and a closed bottom end; an annular wall disposed within the cavity, the annular wall dividing the cavity into a central cavity and an annular cavity, the annular cavity circumferentially surrounding the central cavity; a plurality of radial walls extending from an outer surface of the annular wall to an inner surface of the tubular body, the radial walls dividing the annular cavity into a plurality of subcavities; at least one oral care implement disposed within each of the subcavities; and a cover coupled to at least one of the tubular body and the annular wall so as to enclose a top end of the annular cavity.

In another embodiment, the invention can be a package of oral care implements comprising: an inner annular wall forming a central cavity about a longitudinal axis; an outer annular wall circumferentially surrounding the inner annular wall so as to form an annular cavity between an outer surface of the inner annular wall and an inner surface of the outer annular wall; a floor enclosing a bottom end of the annular cavity; a plurality of radial walls extending from the outer surface of the inner annular wall to the inner surface of the outer annular wall, the radial walls dividing the annular cavity into a plurality of subcavities; at least one oral care implement disposed within each of the subcavities; and an annular cover rotatably coupled to at least one of the inner annular wall and the outer annular wall so as to enclose a top end of the annular cavity, the cover comprising a central opening that forms a passageway to the internal cavity from an external environment and a dispensing opening that forms a passageway into one of the subcavities from the external environment.

In yet another embodiment, the invention can be a method of using an oral care implement comprising: a) obtaining a package of oral care implements, the package comprising a tubular body having a cavity, an open top end and a closed bottom end; an annular wall disposed within the cavity, the annular wall dividing the cavity into a central cavity and an annular cavity, the annular cavity circumferentially surrounding the central cavity; an annular cover rotatably coupled to at least one of the tubular body and the annular wall so as to enclose a top end of the annular cavity, the annular cover comprising a central opening that forms a passageway into the central cavity from an external environment and a dispensing opening that forms a passageway into a portion of the annular cavity from the external environment; and a plurality of oral care implements disposed within the annular cavity; b) rotating the annular cover until the dispensing opening is aligned with a portion of the annular cavity containing the oral care implement; and c) removing the oral care implement from the annular cavity via the dispensing opening.

In still another embodiment, the invention can be a method of using an oral care implement comprising: a) obtaining a package of oral care implements, the package comprising a tubular body having a first cavity and a second cavity, the first cavity separated from the second cavity by at least one wall, the first cavity having an open top end and a closed bottom end, wherein the oral care implements are positioned within the first cavity and a cover encloses the open top end of the first cavity; and b) removing one of the oral care implements from the first cavity.

In a further embodiment, the invention can be a method of using an oral care implement comprising: a) obtaining a package of oral care implements, the package comprising a tubular body having a plurality of subcavities, wherein each of the subcavities comprises a closed bottom end, an open top end, and at least one of the oral care implements positioned therein, and a cover that encloses the open top ends of the subcavities and allows the subcavities to be selectively opened; b) opening one of the subcavities by manipulating the cover, and c) removing the oral care implement from the opened subcavity.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of the exemplary embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," "secured" and similar refer to a relationship wherein structures are secured or attached to one another either directly or indirectly through intervening structures, as well as both movable or rigid attachments or relationships, unless expressly described otherwise. Moreover, the features and benefits of the invention are described by reference to the exemplary embodiments illustrated herein. Accordingly, the invention expressly should not be limited to such exemplary embodiments, even if indicated as being preferred. The discussion herein describes and illustrates some possible non-limiting combinations of features that may exist alone or in other combinations of features. The scope of the invention is defined by the claims appended hereto.

Figure 1:
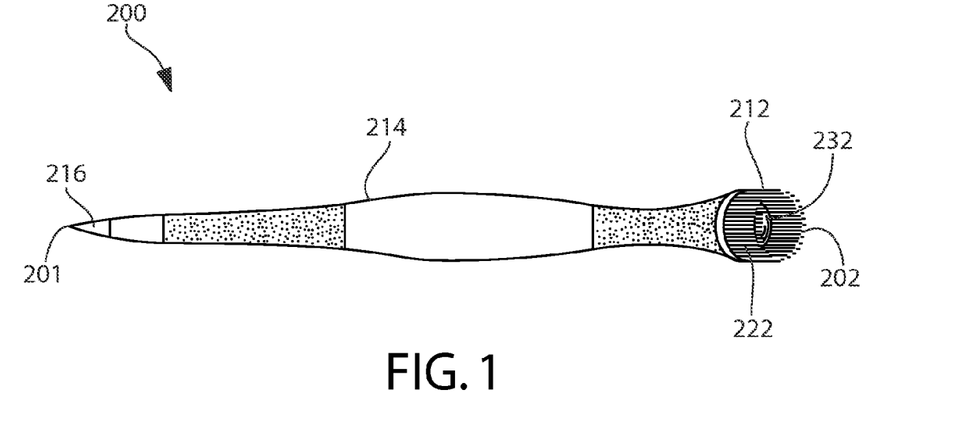
FIG. 1 is a front view of an oral care implement in accordance with one embodiment of the present invention.
Figure 2:
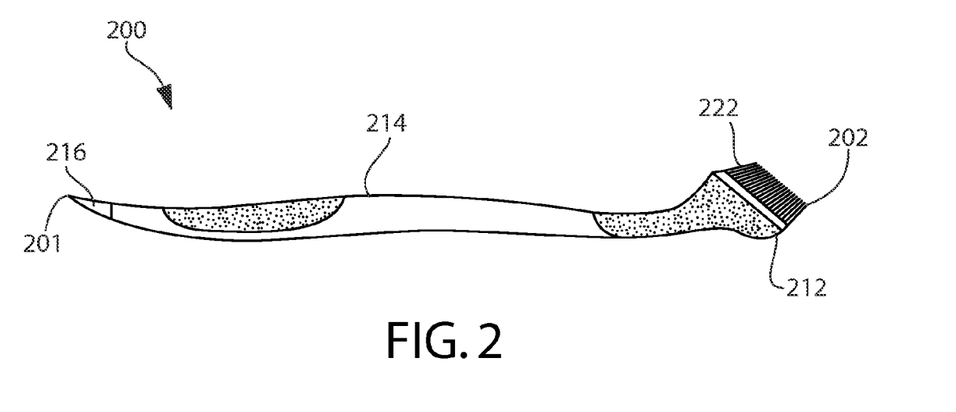
FIG. 2 is a side view of the oral care implement of FIG. 1.

Referring to FIGS. 1 and 2, one embodiment of an oral care implement 200 that is particularly suited for use with the present invention is exemplified. As will become apparent from the discussion below, it is preferred that the oral care implement 200 be packaged in a manner that protects the oral care implement 200 against moisture and/or humidity. The oral care implement 200 extends from a proximal end 201 to a distal end 202 and includes a head 212 and a handle 214. The head 212 may either be a refill head that is removably connected to the handle 214 or a structure that is permanently connected to the handle 214. The majority of the handle 214 and a portion of the head 212 may be molded from a variety of rigid materials, including without limitation plastics, resins and the like. One suitable rigid material is polypropylene. However, other rigid materials may be used as would be known to persons skilled in the art.

In the illustrated embodiment, the proximal end 201 of the handle 214, which is opposite the end to which the head 212 is connected, comprises an oral care accessory, which in the exemplified embodiment is a toothpick 216. The toothpick 216 is preferably formed of a resilient and soft thermoplastic elastomer. As with the head 212, the toothpick 216 may be a refill toothpick that is removably connected to the handle 214 or may be permanently connected to the handle 214. The toothpick 216 provides a mechanism for spot cleaning between teeth. Forming the toothpick 216 of a soft thermoplastic elastomer provides for a more comfortable interproximal cleaning between the teeth. The toothpick 216 could, however, be made of a stiff, rigid material similar to the main portion of the handle 214, or could simply be a rubber or elastomeric pick adhered or otherwise mounted to the end of the handle 214. Alternatively, a different accessory, such as a strip of dental floss or a tongue cleaning element, may be attached to the proximal end 201 of the handle 214. Moreover, in certain embodiments of the invention, the handle 214 may not include an accessory or may include multiple accessories.

The head 212 comprises a cleaning element block 222. The cleaning element block 222 comprises a plurality of bristles extending from the head 212. The bristles of the cleaning element block 222 may be of any desired shape. For example, the bristles could be of cylindrical shape having a uniform diameter throughout their length. Alternatively, the bristles could taper from the root where they extend from the head 212 to their outer cleaning ends.

Furthermore, the dimensions of the various components of the oral care implement 200 are preferably small. Thus, for example, each bristle of the cleaning element block 222 may extend outwardly from the outer surface of the head 212 a distance no greater than 10 mm and preferably no greater than 8 mm and most preferably no greater than 6 mm. Where tapered cleaning elements are used, the root diameter may be no greater than 1.5 mm, more preferably between 0.5 mm and 1 mm, and most preferably no greater than 0.3 mm. The diameter could then decrease in size with distance from the head 212. Preferably, the length of the entire oral care implement 200 is no greater than 5 inches, more preferably no greater than 4 inches and most preferably in the range of 2 to 4 inches.

A central portion of the head 214, which is surrounded by the cleaning element block 222, comprises a depression or cavity for retaining a rupturable gel capsule or bead 232. The gel capsule 232 is filled with an oral care material, such as a fluidic solution, for cleaning or otherwise providing health benefits to a user's teeth. The oral care material may be toothpowder, toothpaste, tooth cleaning gel, mouthwash or a similar dentifrice or oral hygiene product, or a combination of the same. The gel capsule 232 is moisture-sensitive and should be protected against high humidity environments in order to prevent premature rupture. In other words, the gel capsule 232, or at least a portion thereof, is susceptible to degradation when subjected to a high humidity atmosphere as it has been discovered that moisture in the air in a high humidity environment can degrade the integrity of the gel capsule 232. Therefore, it is desirable to package the oral care implement 200 in a manner that protects the gel capsule 232 from humidity and liquid moisture prior to use.

The gel capsule 232 holds and applies an oral care material onto the cleaning element block 222 of the oral care implement head 212, and ultimately to a user's teeth and oral care surfaces. As mentioned above, the oral care material may be toothpaste, a gel, a mouthwash, or a similar dentifrice or oral hygiene product, or a combination of the same. Preferably, the gel capsule 232 is a liquid-filled gel capsule having a shell comprising frangible, thin walls that easily rupture or burst when rubbed against the teeth. In a preferred embodiment, the gel capsule 232 degrades when subjected to moisture and, thus, dissolves when mixed with the saliva of a user. As the saliva of a user degrades and dissolves the walls of the gel capsule 232, the oral care solution held therein is excreted. While the degradation of the gel capsule 232 is a desired characteristic for effectuating end use of the oral care implement 200 by the consumer, the moisture-driven degradation of the gel capsule 232 may present issues with respect to properly preserving the integrity of the gel capsule 232 during product manufacturing, packaging, shipping and display in retail stores.

The gel capsule 232, or at least a portion thereof, is susceptible to degradation when subjected not only to direct contact with liquid water but also to prolonged exposure to atmospheres having a high humidity level. It has been discovered that a high humidity environment can degrade the integrity of the gel capsule 232 and prematurely expel the oral care material or cause the oral care material to dry up. Of course, the exact humidity levels and exposure times that will result in the degradation of the gel capsule 232 will be determined on a case-by-case basis, considering such factors as the type of gel capsule 232 being used, the type of oral care material, and the thermal cycling to which the oral care implement 200 is subjected. In view of the foregoing, it is desirable that the gel capsule 232 (and potentially the entire oral care implement 200) be placed in a package that forms a hermetically sealed cavity in which at least the gel capsule 232 of the oral care implement 200 is disposed, thereby protecting the gel capsule 232 from external moisture which can be in the form of high humidity atmosphere or liquid water.

In one preferred embodiment of the present invention, the entire structure of the oral care implement 200, including the head 212, the handle 214, and the toothpick 216, is molded as one integral structure, using a conventional two-component injection molding operation typically used in the manufacture of oral care implements. This enables the oral care implement 200 to be economically and quickly manufactured. Although the oral care implement 200 may be constructed in a wide variety of sizes, shapes and relative dimensions, it is preferred that the oral care implement 200 have a small profile so that it is easily portable and can be discreetly used. In one embodiment, it is preferred that the head 212 be small enough to cover a single tooth at a time and that the handle 214 be substantially thinner than conventional, everyday oral care implement handles.

Since the oral care implement 200 is intended to be both small and lightweight, it is preferred that the oral care implement 200 weigh no more than 3 grams in certain embodiments. The small size allows the oral care implement 200 to be held completely within the palm of an adult user's hand. The head 212 is preferably sized to correspond to the size of an individual tooth or an individual tooth and the interproximal areas. While the head 212 could be made in any suitable shape, it is preferably of circular or oval shape and has a maximum lateral dimension or diameter of no greater than 13 mm, preferably no greater than 12 mm and most preferably no greater than 11 mm. Of course, the oral care implement 200 is not limited to any specific dimensions or shapes.

It is to be understood that the present invention is not limited to the above-described oral care implement 200. While the inventive package 100 will be described in combination with a plurality of the oral care implements 200, it is to be understood that other oral care implements can be packaged as discussed below. The package 100 is in no way limited to the structure of the oral care implement 200 unless specifically stated in the claims. In the exemplary embodiment, the oral care implement disposed within the package 100 is one which is disposable, has a pre-applied oral care material, and must be protected against moisture. However, in certain other embodiments, a conventional toothbrush or any other type of oral care implement may be disposed within the package, irrespective of whether it must be protected against moisture and/or contains a pre-applied oral care material. As used herein, pre-applied means that the oral care material is associated with the oral care implement as-packaged for sale. Similarly, while the inventive package 100 will be described in combination with a plurality of the oral care implements 200, it is to be understood that articles other than oral care implements can be packaged as discussed below. For example, the inventive package 100 may be used to package candies, medicines, vitamins, toothpicks, and other articles suitable for storage in the package 100. In some embodiments, the articles stored in the package 100 may include an outer protective packaging material, such as wrappers. In these embodiments, the wrappers may be disposed of in the package 100 as described below.

Figure 3:
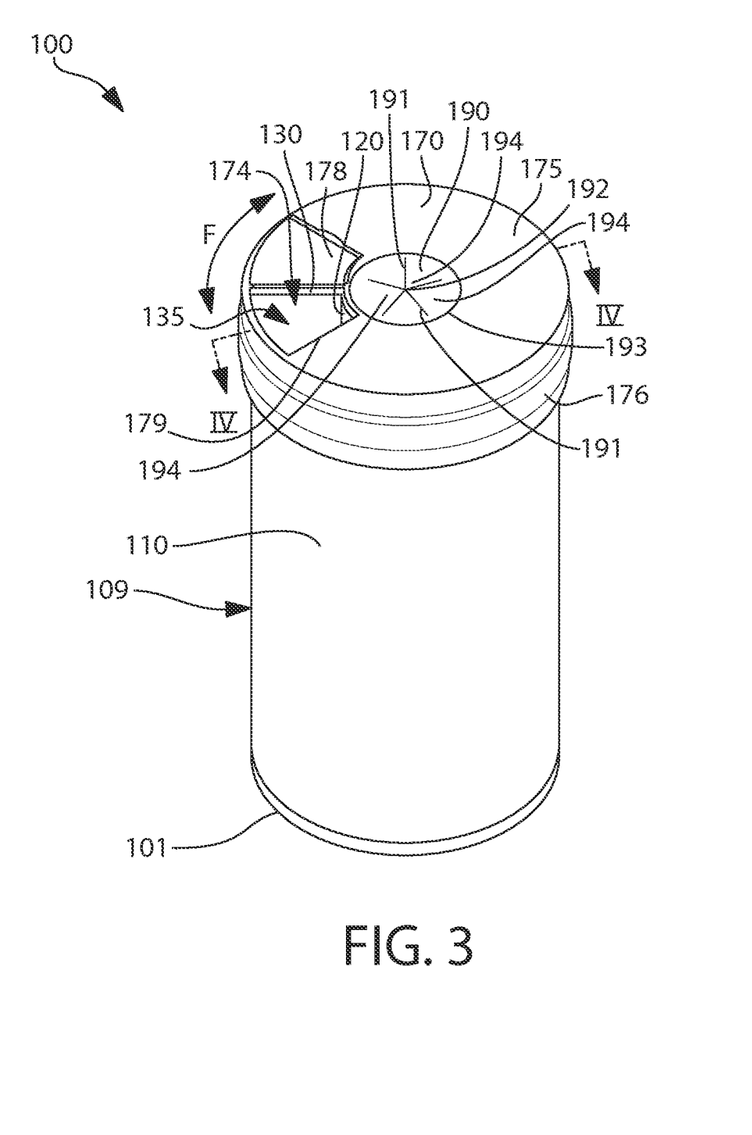
FIG. 3 is a perspective view of a package of oral care implements in accordance with one embodiment of the present invention.
Figure 4:
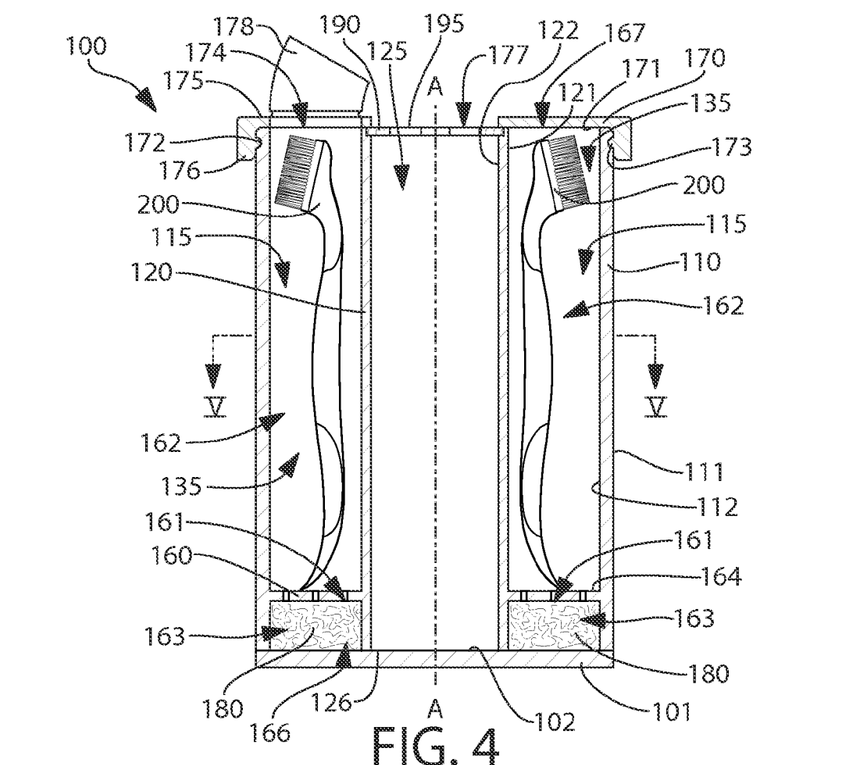
FIG. 4 is a cross-sectional view taken along line IV-IV of FIG. 3.
Figure 5:
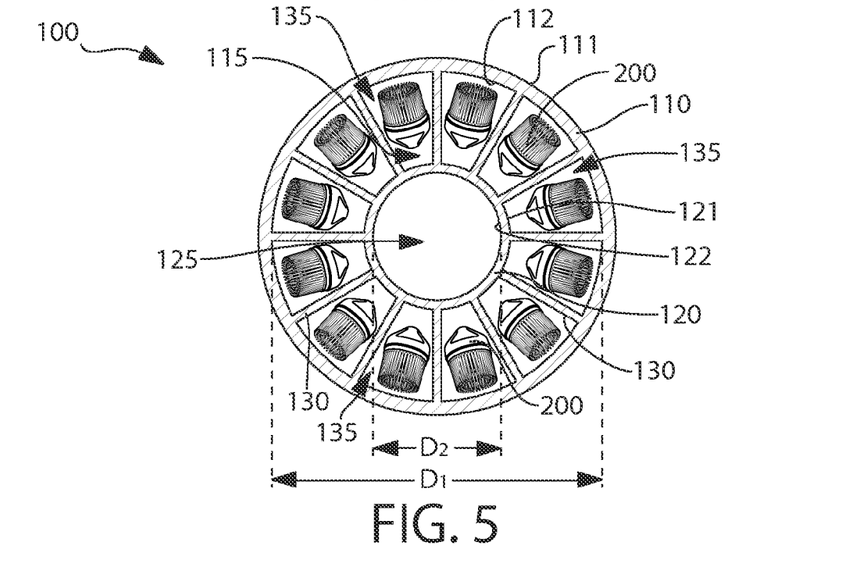
FIG. 5 is a cross-sectional view taken along line V-V of FIG. 4.

Referring to FIGS. 3-5 concurrently, a package 100 containing a plurality of the oral care implements 200 is illustrated. The package 100 keeps moisture out of the cavities containing the oral care implements 200 so that the oral care material, which is in the form of the gel capsule 232, is protected from degradation due to humidity and/or moisture. Of course, in embodiments where the oral care implements contained within the package 100 do not need to be protected against moisture degradation, the package 100 need not be moisture sealed.

The package 100 generally comprises a tubular body 109 and an inner annular wall 120. The tubular body 109 comprises an outer annular wall 110 that circumferentially surrounds the inner annular wall 120 and a floor 101 enclosing a bottom end of the tubular body 109. As will be described in detail below, in the exemplified embodiment, the outer and inner annular walls 110, 120 are formed as a unitary structure and the floor 101 is coupled to the outer and/or inner annular walls 110, 120 during a second manufacturing step. Of course, the entire package 100 can be an integrally formed structure or can be formed from a greater number of individual components that are subsequently assembled.

The inner annular wall 120 comprises an outer surface 121 and an inner surface 122. Similarly, the outer annular wall 110 comprises an outer surface 111 and an inner surface 112. A central cavity 125 is formed between the inner surface 122 of the inner annular wall 120 and a top surface 102 of the floor 101. The central cavity 125 extends along a longitudinal axis A-A, which is also the central axis of the inner and outer walls 110, 120. In certain alternative embodiments, the floor 101 may not enclose a bottom end 126 of the central cavity 125. In such embodiments, the bottom end 126 of the central cavity 125 may be open thereby forming a passageway through the entirety of the package 100.

The outer annular wall 110 circumferentially surrounds the inner annular wall 120 in a spaced apart manner so that an annular cavity 115 is formed between the outer surface 121 of the inner annular wall 120 and the inner surface 112 of the outer annular wall 110. The annular cavity 115 circumferentially surrounds the central cavity 125 and is enclosed at its bottom end by the floor 101. In the exemplified embodiment, the inner and outer annular walls 110, 120 are concentrically arranged about the longitudinal axis A-A. However, in alternative embodiments, one or both of the inner and outer annular walls 110, 120 may be non-concentric to the longitudinal axis A-A.

In a desired embodiment, the annular cavity 115 is hermetically sealed to prevent moisture from entering. As will be understood from the description below, it may be desirable that the annular cavity 115 be enclosed by the floor 101 irrespective of whether or not the central cavity 125 is also enclosed by the floor 101.

In the exemplified embodiment, the inner and outer annular walls 110, 120 have a circular transverse cross-sectional profile. However, the invention is not so limited and in alternative embodiments, the inner and outer annular walls 110, 120 can have transverse cross-sectional profiles of almost any shape, including without limitation rectangular, oval, triangular, or otherwise polygonal. Moreover, while the inner and outer annular walls 110, 120 are exemplified having the same transverse cross-sectional profile shape, in other embodiments, the inner and outer annular walls 110, 120 may have different transverse cross-sectional profile shapes. For example, the outer annular wall 110 may have a circular transverse cross-sectional profile while the inner annular wall 120 may have a rectangular transverse cross-sectional profile.

The package 100 further comprises a plurality of radial walls 130 extending radially outward from the outer surface 121 of the inner annular wall 120 to the inner surface 112 of the outer annular wall 110. The radial walls 130 divide the annular cavity 115 into a plurality of subcavities 135 that are arranged circumferentially about the longitudinal axis A-A. In the illustrated embodiment, the package 100 has twelve radial walls 130 that divide the annular cavity 125 into twelve equally sized subcavities 135. Of course, the invention is not so limited and more or less than twelve radial walls 130 may be provided to divide the annular cavity 125 into more or less than twelve subcavities 135. Furthermore, in certain embodiments the radial walls 130 may divide the annular cavity 125 into a plurality of subcavities 135 of different sizes. The number and size of the subcavities 135 are in no way limiting of the present invention.

In the exemplified embodiment, each of the subcavities 135 is sized and configured to contain a single one of the oral care implements 200 therein. Thus, in one embodiment of the invention, the distance between the inner surface 112 of the outer annular wall 110 and the outer surface 121 of the inner annular wall 120 is approximately between 6-20 mm, and more preferably between 10-15 mm. Of course, the size of the subcavities 135 may be larger or smaller than the ranges discussed herein in order to accommodate larger or smaller oral care implements, or to accommodate more than a single one of the oral care implements 200 therein. In addition, in the exemplified embodiment, each of the subcavities 135 contains the same oral care implement 200, however, it is contemplated that different oral care implements may be contained in the subcavities 135.

In certain embodiments, each of the subcavities 135 may be sized and configured to contain multiple oral care implements 200 therein. In those embodiments, the subcavities 135 may be further divided into sub-subcavities by another wall and/or spacer. Because the oral care implements 200, which contain the moisture sensitive oral care material, are disposed within the subcavities 135, it is desired that each of the subcavities 135 be separately hermetically sealed from one another so as to maintain a moisture-free environment within each of the subcavities 135 prior to use of the particular oral care implement 200 within that subcavity 135.

The package 100 further comprises an annular cover 170. In the exemplified embodiment, the annular cover 170 is rotatably coupled to the outer annular wall 110. However, the invention is not so limited and the annular cover 170 can be rotatably coupled to either the outer annular wall 110 and/or the inner annular wall 120 as desired. Furthermore, it should be understood that the annular cover 170 is considered to be coupled to the outer or inner annular walls 110, 120 irrespective of whether the annular cover 170 is directly or indirectly coupled to the outer or inner annular walls 110, 120. For example, in certain embodiments, the annular cover 170 can be indirectly coupled to the outer or inner annular walls 110, 120 via a flange or other structure coupled to the outer and/or inner annular walls 110, 120 and/or to the annular cover 170. While the annular cover 170 is referred to as an annular cover, it is understood that the cover 170 needs not be annular.

The annular cover 170 comprises a top plate 175 and an annular skirt 176. In the exemplified embodiment, the outer annular wall 110 comprises an annular recess 172 and the annular skirt 176 of the annular cover 170 comprises an annular flange 173. When the package 100 is assembled, the annular flange 173 of the annular cover 170 fits within the annular recess 172 of the outer annular wall 110, thereby enclosing and hermetically sealing a top end of the annular cavity 115. The annular flange 173 may comprise a gasket to ensure that the seal between the annular cover 170 and the inner or outer annular walls 110, 120 is hermetic so that moisture from the external environment cannot penetrate into the annular cavity 115. Any type of gasket may be used, including without limitation composite gaskets, flange gaskets, solid metal gaskets, spiral wound gaskets, corrugated gaskets, encapsulated gaskets, fiber seal rings and foam gaskets. In other embodiments, a hermetic seal may be achieved in a wide variety of manners via proper mating at the subject interface(s).

The annular flange 173 and the annular recess 172 are cooperatively engaged so that the annular cover 170 is able to rotate 360° in either direction about the longitudinal axis A-A. Of course, the invention is not so limited and other methods of attaching the annular cover 170 to the outer or inner annular walls 110, 120 so that the annular cover 170 can achieve a 360° rotation about the longitudinal axis A-A can be used.

The annular cover 170 comprises a central opening 177 that forms a passageway into the central cavity 125 from an external environment. The annular cover 170 encloses only the annular cavity 115, leaving the central cavity 125 unobstructed. The annular cover 170 seals the annular cavity 115 from the external environment so that moisture and humidity in the external environment cannot enter into the annular cavity 115. As discussed above, at least one oral care implement 200 is disposed within each of the subcavities 135 of the annular cavity 115. Thus, sealing the annular cavity 115 (and, hence, the subcavities 135) prevents moisture and/or humidity from degrading the oral care material of the oral care implements 200 as discussed above. It is preferable that the annular cavity 115 be hermetically sealed from the external environment when the annular cover 170 is coupled to the outer and/or inner annular walls 110, 120.

The annular cover 170 also comprises a dispensing opening 174 that forms a passageway from the external environment into a portion of the annular cavity 115. Specifically, the dispensing opening 174 is sized to provide a passageway from the external environment into a single one of the plurality of subcavities 135 at a time. By rotating the annular cover 170 as described above, the dispensing opening 174 will rotate about the longitudinal axis A-A so that it can be selectively positioned so as to be aligned with a top end of each of the plurality of subcavities 135, one at a time. Thus, a user can gain access to each of the plurality of subcavities 135, one at a time, by rotating the annular cover 170. In this way, all of the subcavities 135 will remain sealed from the external environment except for the subcavity 135 that the dispensing opening 174 is positioned above. It should be noted, however, that in certain embodiments, the annular cavity 115 (and thus the subcavities 135) may not be hermetically sealed.

The annular flange 173 frictionally engages the annular recess 172 when the annular cover 170 is attached to the inner and/or outer annular walls 110, 120 as described above. As such, the annular cover 170 is not able to rotate without a user applying a rotational force F in the direction of the arrows as shown in FIG. 3. In other words, there is enough friction between the annular recess 172 and the annular flange 173 so that the annular cover 170 will not move freely without application of a rotational force F to the annular cover 170.

In order to maintain all of the subcavities 135 in a sealed environment until a user desires to gain access to one of the subcavities 135, a lid 178 is provided that covers (and potentially seals) the dispensing opening 174. In the exemplified embodiment, the lid 178 is attached to the cover 170 by a hinge. More specifically, in the exemplified embodiment the hinge is a living hinge. Of course, the invention is not so limited and the lid 178 may be coupled to the cover 170 in other ways as would be known to persons skilled in the art, including without limitation, a butt hinge, a butterfly hinge, a flush hinge, a barrel hinge, a concealed hinge, a continuous hinge, adhesion, thermal welding, tight-fit, threaded engagement, fasteners, combinations thereof or the like. Furthermore, in other embodiments the lid 178 may be completely removable from the annular cover 170 such that it can be used to cover the dispensing opening 174 by a press-fit, snap-fit or other type of connection as would be known to persons skilled in the art.

The lid 178 is sized and shaped to correspond with the size and shape of the dispensing opening 174. In the exemplary embodiment, the lid 178 and dispensing opening 174 have a sector-like shape with two straight sides that diverge from each other with distance from the inner annular wall 120 and two arcuate sides connecting the two straight sides. Of course, the invention is not so limited and the lid 178 and dispensing opening 174 may take on other known shapes as long as the lid 178 is sized and shaped to close the dispensing opening 174 (and potentially seal the annular cavity 115 from external moisture) as discussed above.

In the exemplary embodiment illustrated in FIG. 3, the lid 178 opens from a side 179 of the dispensing opening 174. Of course, the invention is not so limited. In certain other embodiments, the lid 178 may open from the front of the dispensing opening 174 or in other manners as would be known to persons skilled in the art. A second embodiment illustrating an alternative mechanism for opening the lid 178 will be discussed below with reference to FIG. 6.

The lid 178 is movable between: (1) a closed position wherein the lid 178 encloses the dispensing opening 174, thereby enclosing the annular cavity 115 and each of the plurality of subcavities 135 from the external environment; and (2) an open position that exposes one of the subcavities 135 of the annular cavity 115 to the external environment. In FIGS. 3 and 4, the lid 178 is illustrated in the open position. In certain embodiments, the lid 178 will hermetically seal the dispensing opening 174 when in the closed position.

The package 100 also comprises a disposal cap 190 having a top surface 195. The disposal cap 190 substantially closes the central opening 177. However, it is not necessary that the central opening 177 be completely sealed from the external environment because objects, such as the oral care implements 200 after being used to treat a user's oral cavity, are placed within the central cavity 125 as will be discussed in more detail below. After use, the oral care implements 200 do not need to be protected against moisture or humidity.

In one embodiment, the disposal cap 190 can be formed of a flexible material, such as an elastomer or a thin, flexible plastic material. The flexible material of the disposal cap 190 may be coupled to the annular cover 170. Alternatively, as illustrated in the exemplified embodiment of FIG. 4, the disposal cap 190 can be coupled to the inner surface 122 of the inner annular wall 120. As illustrated, the disposal cap 190 may fit within an indentation or recess in the inner surface 122 of the inner annular wall 120. In certain embodiments, the disposal cap 190 is removable such that it can be attached to and detached from the annular cover 170 or the inner annular wall 120.

The disposal cap 190 has a plurality of slits 191 extending radially from a center 192 of the disposal cap 190 towards a peripheral edge 193 of the disposal cap 190. However, the slits 191 do not extend the entire radius of the disposal cap 190 and therefore do not extend all the way to the peripheral edge 193 of the disposal cap 190. The slits 191 create a plurality of flaps 194 that collectively form the disposal cap 190.

As noted above, the disposal cap 190 is formed of a flexible material. As such, if a downward force is applied to the top surface 195 of the disposal cap 190 at the center 192 of the disposal cap 190, the plurality of flaps 194 will separate along the slits 191 and create a passageway into the central cavity 125. This enables objects, such as the oral care implements 200 after use, to be discarded in the central cavity 125. Thus, the central cavity 125 acts as a wastebasket for discarding used oral care implements 200. Furthermore, the disposal cap 190 hides the used oral care implements 200 disposed within the central cavity 125 from view while also preventing the used oral care implements 200 from falling out of the central cavity 125. Of course, it should be understood that because the oral care implements 200 within the central cavity 125 do not need to be moisture sealed, the disposal cap 190 may be omitted altogether in certain alternative embodiments.

As noted above, the central cavity 125 is intended to contain the oral care implements 200 after use. Collectively, the central cavity 125 and the annular cavity 115 have a diameter $D_1$ while the central cavity alone 125 has a diameter $D_2$. In one embodiment, the ratio of the diameter $D_1$ to the diameter $D_2$ is approximately between about 1.2:1 to about 1.4:1, and preferably about 1.3:1. As such, the diameter $D_2$ of the central cavity 125 is between approximately 70% to approximately 85%, and preferably approximately 75% of the diameter $D_1$ of the combined central cavity 125 and annular cavity 115.

By designing the package 100 so that the central cavity 125 is larger than the annular cavity 115, all of the oral care implements 200 within the subcavities 135 of the annular cavity 115 can be disposed within the central cavity 125 after use. Thus, the central cavity 125 is preferably sized to contain all of the oral care implements 200 that are positioned within the subcavities 135 at one time. In this way, once all of the oral care implements 200 have been used and disposed in the central cavity 125, the entire package 100 can be thrown away. Alternatively, the central cavity 125 can simply be emptied and the subcavities 135 refilled with the oral care implements 200 and resealed.

The package 100 may be designed to be positioned in a cup holder of a user's vehicle. As such, the diameter $D_1$ at a bottom end 166 of the package 100 is preferably between 60-80 mm. However, the package 100 may take on a tapered shape (not shown) such that the diameter $D_1$ of the combined central cavity 125 and annular cavity 115 is larger at a top end 167 of the package 100 than at the bottom end 166 of the package 100. The outer annular wall 110 may be tapered so that only the size of the annular cavity 115 becomes greater towards the top. The central cavity 125 may have a constant diameter, or may also be tapered. Such a tapered contour enables the package 100 to fit within the cup holder of a vehicle while providing ample space within the top end 167 of the annular cavity 135 for the head 212 and cleaning element block 222 of the oral care implements 200 to fit therein.

Referring now to FIG. 4, the package 100 further comprises a transverse plate 160 positioned within each of the subcavities 135 that separates each of the subcavities 135 into an upper chamber 162 and a lower chamber 163. Conceptually, the package 100 can be considered to include a single transverse plate 160 extending radially across the entirety of the annular cavity 115. In the exemplary embodiment, the transverse plate 160 does not extend into the central cavity 125. Thus, the transverse plate 160 is an annular plate that extends from the outer surface 121 of the inner annular wall 110 to the inner surface 112 of the outer annular wall 120. The upper chamber 162 extends between a bottom surface 171 of the annular cover 170 and a top surface 164 of the transverse plate 160. Similarly, the lower chamber 163 extends between a bottom surface 165 of the transverse plate 160 and the top surface 102 of the floor. In the exemplified embodiment, the transverse plate 160 is integrally formed as a unitary part with the inner and outer annular walls 110, 120. The manufacturing process involved in creating the package 100 will be described in greater detail below.

In the exemplified embodiment, the transverse plate 160 comprises a plurality of openings 161, each of which provides a passageway between the upper and lower chambers 162, 163 of the subcavities 135. In other words, for each subcavity 135, air within the upper chamber 162 is able to flow downward into the lower chamber 163 through the openings 161 and vice versa. As will be better understood from the discussion below, it is preferable that there is at least one opening 161 in a portion of the transverse plate 160 that is disposed within each of the plurality of subcavities 135. This will enable air to circulate between the upper and lower chambers 162, 163 in each of the subcavities 135. In the exemplified embodiment, there are three openings 161 in the transverse plate 160 in each of the subcavities 135. However, the invention is not so limited and there can be more or less openings 161 in the transverse plate 160 as desired. Furthermore, it should be understood that in certain other embodiments, the transverse plate 160 can be omitted altogether.

In the exemplified embodiment, a desiccant 180 is disposed in the lower chamber 163 of the annular cavity 115. The desiccant 180 may be any material that is known to induce or sustain a state of dryness in its local vicinity in a moderately well-sealed container. The dessicant 180 may be, for example without limitation, silica gel, calcium sulfate, calcium chloride, montmorillonite clay, molecular sieves, rice, salt or the like. Other desiccants that are now known or later discovered that can sustain a state of dryness within a sealed container while not transmitting any toxins to the oral care implements 200 disposed within the subcavities 135 may be used.

The oral care implements 200 are disposed in the upper chamber 162 of the annular cavity 115. Thus, the entire package 100 only needs to be large enough in height to contain the oral care implements 200, which may be as small as 2 to 4 inches, and the desiccant 180, which may simply be a layer of salt disposed in the lower chamber 163.

Due to the openings 161 in the transverse plate 160, the desiccant 180 will absorb any moisture within either of the upper and lower chambers 162, 163 because the air within the subcavities 135 will freely flow between the upper and lower chambers 162, 163 through the openings 161 in the transverse plate 160. Thus, the desiccant 180 will remove excess humidity that would otherwise degrade or potentially destroy the oral care implements 200 within the upper chamber 162.

It is preferred that the oral care implements 200 be placed in the package 100 at a relative humidity level that is less than approximately 70% at room temperature, preferably less than approximately 60% at room temperature, more preferably less than approximately 50% at room temperature, and most preferably less than approximately 40% at room temperature in order to avoid degradation of the gel capsules 232. However, in certain embodiments, even if an atmosphere having a higher humidity is initially trapped within the subcavities 135, the desiccant 180 in the lower chamber 163 will be able to absorb the excess moisture without degrading the gel capsule 232 of the oral care implement 200. However, the subcavities 135 are air-tight in order to prevent further exposure of the gel capsule 232 of the oral care implement 200 to moisture, thereby keeping the gel capsule 232 intact.

The outer and inner annular walls 110, 120, the transverse plate 160, the floor 101 and the annular cover 170 can be formed of any type of material as would be known to persons skilled in the art. Specifically, the material may be a metal or metal alloy, or a thermoplastic such as for example polypropylene, polyethylene, polystyrene, or polyvinyl chloride. Of course, the invention is not so limited and other materials as would be known to persons skilled in the art can be used.

The package 100 can be formed in a multi-step process. Specifically, in one embodiment, the inner and outer annular walls 110, 120 and the transverse plate 160 are formed in a single step injection molding process. After the outer and inner annular walls 110, 120 and the transverse plate 160 are formed, the lower chamber 163 is filled with the desiccant

180. Then, after the desiccant 180 is properly positioned, the floor 101, which is in the form of a plate, is connected to the inner and outer annular walls 110, 120 so as to enclose the bottom ends of the inner and outer annular walls 110, 120.

The floor 101 can be created in a second injection molding step and then attached or coupled to the inner and outer annular walls 110, 120 at a later stage of the manufacturing process. The coupling of the floor 101 to the inner and outer annular walls 110, 120 can be achieved by any suitable technique known in the art, including without limitation thermal welding, a tight-fit assembly, a coupling sleeve, adhesion, fasteners or the like. It should be understood that as discussed above, in certain embodiments the floor 101 only encloses the bottom end of the annular cavity 115 while leaving the bottom end 126 of the central cavity 125 exposed. This is possible because the central cavity 125 does not need to be sealed in an air-tight fashion as discussed above. Furthermore, it should be understood that the various components of the package 100 may be formed by methods other than molding, such as, for example, milling, machine, or other suitable process.

As discussed above, the package 100 is preferably sized so that it can fit within a vehicle cup holder. Thus, a user will have oral care implements 200 available for use when the user is driving in the vehicle. Of course, the invention is not so limited and the package 100 can take on other shapes and sizes than those disclosed herein.

Referring again to FIGS. 3-5 concurrently, a method of using the package of oral care implements 100 will be described. The package 100 will be obtained by user, with at least one oral care implement 200 disposed within each of the plurality of subcavities 135 of the annular cavity 115. The lid 178 will be in a closed position so that the dispensing opening 174 is closed and the subcavities 135 are substantially sealed from the external environment. The user will rotate the annular cover 170 until the dispensing opening 174 is positioned above (i.e., aligned with) one of the subcavities 135. The user can rotate the annular cover 170 by gripping the outer surface 111 of the outer annular wall 110 and turning the annular cover 170 in a rotational direction around the longitudinal axis A-A. The annular cover 170 will freely rotate upon application of the rotational force F. Once the dispensing opening 174 is positioned above one of the subcavities 135, the lid 178 can be moved from the closed position to the open position. After the lid 178 is opened, one of the subcavities 135 will be exposed to the external environment through the dispensing opening 174. Although one of the subcavities 135 will be exposed, the remainder of the subcavities 135 will remain sealed from the external environment in order to prevent moisture from entering into the remainder of the subcavities 135.

The user can then remove the oral care implement 200 that is disposed within the exposed subcavity 135 and use the oral care implement 200 to clean the user's teeth and/or soft tissue surfaces. After use, the oral care implement 200 can be discarded in the central cavity 125 by pushing the used oral care implement 200 into the central cavity 125 through the disposal cap 190. The user can then close the lid 178 in order to ensure that the subcavities 135 remain moisture-sealed. This process can be repeated until all of the oral care implements 200 have been removed from their respective subcavities 135, used to clean a user's teeth and discarded in the central cavity 125.

In certain embodiments, especially relating to the method of use, packages having alternative constructions may be used. Specifically, the package may be a tubular body having a first cavity and a second cavity that are separated from one another by at least one wall. In such an embodiment, the first cavity and the second cavity are not limited to the central cavity and annular cavity arrangement discussed above. For example, in certain specific embodiments, the first and second cavities can be semi-cylindrical, par-cylindrical and/or any transverse sectional shape of the tubular body. As with the exemplified embodiment of FIGS. 1-5, the first cavity can have an open top end and a closed bottom end. The oral care implements are positioned within the first cavity, which may or may not be divided into subcavities as desired. The open top end of the first cavity is then substantially enclosed by a cover, which can be the annular cover described above or a simple removable lid. During use, a user can remove one of the oral care implements from the first cavity and then use the oral care implement to treat his or her oral cavity. The oral care implement can be removed from the first cavity by removing or otherwise manipulating the cover and exposing the first cavity. Alternatively, the oral care implement may be removed through an opening in the cover, which is closed by a lid as described above. After removal and use of the oral care implement, the oral care implement is placed into the second cavity for disposal. Thus, the first cavity acts as a storage compartment for the oral care implements prior to use and the second cavity acts as a wastebasket or storage housing for the oral care implements after use.

In still another embodiment relating to the method of use, the package may be a tubular body having a plurality of subcavities formed therein that contain at least one oral care implement. In such an embodiment, the entirety of the package may be formed of the subcavities and a dedicated disposal cavity may be omitted. In such an embodiment, the subcavities can be formed by a rectilinear gridwork of walls. The oral care implements are retrieved from the subcavities as discussed above and used. However, because there is no dedicated disposal cavity, the used oral care implements are placed back into the subcavity from which they were originally stored prior to use.

Figure 6:
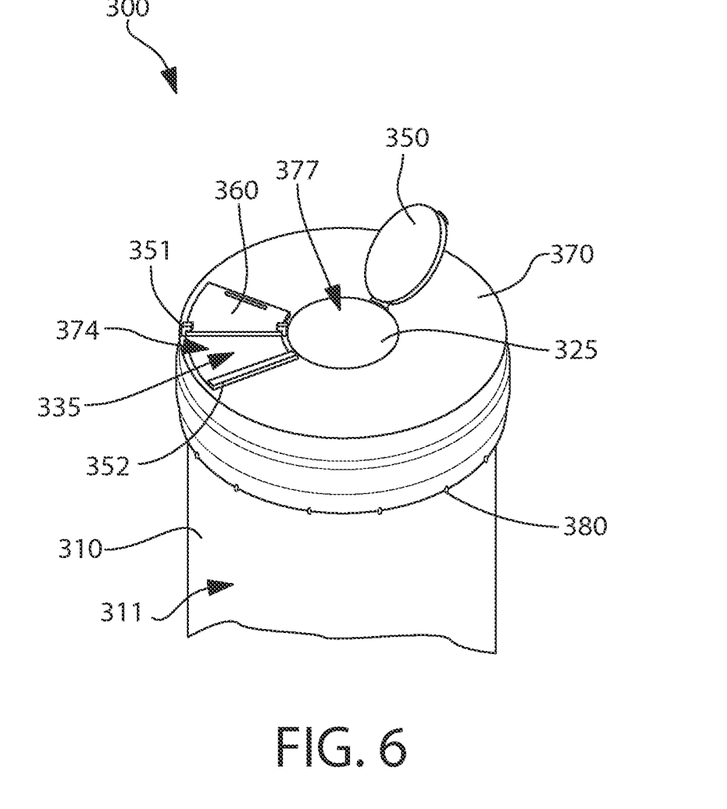
FIG. 6 is a perspective view of an upper portion of a package of oral care implements in accordance with an alternative embodiment of the present invention.

Referring now to FIG. 6, an alternative embodiment of a package 300 of oral care implements is illustrated. The package 300 is identical to the package 100 except that the mechanisms for closing the dispensing opening 174 and the central opening 177 are different and the annular cover 170 has an additional rotation-stop feature. The portions of the package 300 that are the same as portions of the package 100 will be described with the same reference numerals, except that the 300-series of numbers will be used.

The package 300 comprises an annular cover 370 with a central opening 377 that forms a passageway into a central cavity 325. A disposal cap 350 is coupled to the annular cover 370 to close the central opening 377 in the annular cover 370. In the illustrated embodiment, the disposal cap 350 is coupled to the annular cover 370 by a living hinge 351. However, the invention is not so limited and the disposal cap 350 may be coupled to the annular cover 370 by any of the methods discussed above. The disposal cap 350 is able to be press-fit into the central opening 377 to substantially enclose the central cavity 325 from the external environment.

Furthermore, a lid 360 is slidingly coupled to the annular cover 370. The lid 360 is retained on the annular cover 370 by a retaining wall 351. The retaining wall 351 enables the lid 360 to slide between a closed position wherein the lid 360 closes the dispensing opening 374 and hermetically seals an annular cavity 335 from the external environment and an open position wherein the lid 360 does not cover the dispensing opening 374. In FIG. 6, the lid 360 is illustrated in the open position.

The annular cover 370 further comprises a blocking wall 352 that prevents the lid 360 from sliding beyond the dispensing opening 374. Furthermore, the retaining wall 351 is connected to the lid 360 in a manner that prevents the lid 360 from sliding too far in the circumferential direction. In other words, the lid 360 is only capable of sliding in a first circumferential direction just far enough to leave the dispensing opening 374 completely open and exposed and a second circumferential direction just far enough to completely close the dispensing opening 374 so that the lid 360 abuts against the blocking wall 352.

The annular cover 370 further comprises protrusions 380 spaced along the circumference of the annular cover 370. The protrusions 380 correspond with recesses (not shown) in an outer surface 311 of an outer annular wall 310. The recesses are spaced along the circumference of the outer surface 311 of the outer annular wall 310 so that when the protrusions 380 are engaged with and positioned within the recesses, the dispensing opening 374 is positioned directly above a single one of the plurality of subcavities 335. The protrusions 380 can be easily disengaged from the recesses so that the annular cover 370 can be further rotated merely by applying a twisting or rotational force to the annular cover 370. However, the annular cover 370 will temporarily lock in place relative to the outer annular wall 310 when the protrusions 380 are positioned within the recesses so that a user will know when the dispensing opening 374 is positioned directly above a single one of the subcavities 335. It should be understood that although the invention is described with protrusions 380 on the annular cover 370 and the recesses in the outer surface 311 of the outer annular wall 310, in other embodiments the protrusions 380 may extend from the outer surface 311 of the outer annular wall 310 and the recesses may be formed into the annular cover 370. It should be understood that any of the components of the package 300 may be interchanged with a similar component of the package 100. In other words, the elements of the packages 100, 300 can be used in any combination to create a package for oral care implements with desirable features and elements.

As used throughout, ranges are used as shorthand for describing each and every value that is within the range. Any value within the range can be selected as the terminus of the range. While a number of embodiments of the current invention have been described and illustrated in detail, various alternatives and modifications will become readily apparent to those skilled in the art without departing from the spirit and scope of the invention. As various changes could be made in the above methods, compositions and structures without departing from the scope of the invention, it is intended that all matter contained in this application, including all mechanisms and/or modes of interaction described above, shall be interpreted as illustrative only and not limiting in any way the scope of the appended claims.

What is claimed is:

1. A package of articles comprising:
    a tubular body having a cavity, an open top end and a closed bottom end;
    an annular wall disposed within the cavity, the annular wall dividing the cavity into a central cavity and an annular cavity, the annular cavity circumferentially surrounding the central cavity;
    a plurality of radial walls extending from an outer surffice of the annular wall to an inner surface of the tubular body, the radial walls dividing the annular cavity into a plurality of subcavities,
    at least one article disposed within each of the subcavities; and
    an annular cover rotatably coupled to at least one of the tubular body and the annular wall so as to enclose a top end of the annular cavity, the annular cover comprising a central opening, that forms a passageway into the central cavity from an external environment and a dispensing opening that forms a passageway into one of the subcavities from the external environment.

2. The package according to claim 1 further comprising a lid coupled to the annular cover, the lid movable between: (1) a closed position in which the dispensing opening, is sealed; and (2) an open position in which one of the articles can pass through the dispensing opening.

3. The package according to claim 2 wherein the lid is coupled to the annular cover by a living hinge.

4. The package according to claim 1 further comprising a cap that encloses the central opening.

5. The package according to claim 4 wherein the cap is formed of a flexible material having, a plurality of slits extending radially from a center of the cap.

6. The package according to claim 4 wherein the cap is coupled to one of the cover or the annular wall by a living hinge.

7. The package according to claim 1 wherein the annular cover can be selectively rotated relative to the subcavities so that articles from different subcavities can be dispensed via the dispensing opening.

8. The package according to claim 1 wherein when the dispensing opening of the annular cover is aligned with one of the subcavities, the other subcavities remain sealed by the annular cover.

9. The package according to claim 1 further comprising, for each stibcavity, a transverse plate separating the subcavity into an upper chamber and a lower chamber, the transverse plate having at least one opening that forms a passageway from the upper chamber to the lower chamber.

10. The package according to claim 9 wherein each of the subeavities are sealed with respect to one another.

11. The package according to claim 9 wherein, for each subcavity, the article is located in the upper chamber and a desiccant is located in the lower chamber.

12. The package according to claim 7 further comprising a lid that enclosing. the dispensing opening, wherein the subcavities are hermetically sealed with respect to one another and the external environment.

13. The package according to claim 1 wherein the article is an oral care implement.

14. A package of oral care implements comprising:
    a tubular body having a cavity, an open top end and a closed bottom end;
    an annular wall disposed within the cavity, the annular wall dividing the cavity into a. central cavity and an annular cavity, the annular cavity circumferentially surrounding the central cavity;
    a plurality of radial walls extending from an outer surface of the annular wall to an inner surface of the tubular body, the radial walls dividing the annular cavity into a plurality of subcavities;
    at least one oral care implement disposed within each of the subcavities;
    a cover coupled to at least one of the tubular body and the annular wall so as to enclose a top end of the annular cavity; and
    wherein for each subcavity, a transverse plate separating the subcavity into an upper chamber and a lower chamber, the transverse plate having at least one opening that forms a passageway from the upper chamber to the lower chamber.

15. The package according to claim 14, wherein the cover comprises an annular cover comprising a central opening that forms a passageway into the central cavity from an external environment and a dispensing opening that forms a passageway into one of the subcavides from the external environment, the annular cover being rotatably coupled to the at least one of the tubular body and the annular wall.

16. The package according to claim 15 further comprising a lid coupled to the cover, the lid movable between: (1) a closed position in which the dispensing opening is sealed; and (2) an open position in which one of the oral care implements can pass through the dispensing opening.

17. The package according to claim 15 wherein the cover can be selectively rotated relative to the subcavities so that oral care implements from different subcavities can he dispensed via the dispensing opening.

18. A package of oral care implements comprising:
an inner annular wall forming a central cavity about a longitudinal axis;
an outer annular wall circumferentially surrounding the inner annular wall so as to form an annular cavity between an outer surface of the inner annular wall and an inner surface of the outer annular wall;
a floor enclosing a bottom end of the annular cavity;
a plurality of radial walls extending from the outer surface of the inner annular wall to the inner surface of the outer annular wall, the radial walls dividing, the annular cavity into a plurality of subcavities;
at least one oral care implement disposed within each of the subcavities; and
an annular cover rotatably coupled to at least one of the inner annular wall and the outer annular wall so as to enclose a top end of the annular cavity, the annular cover comprising a central opening that forms a passageway to the central cavity from an external environment and a dispensing opening that forms a passageway into one of the subcavities from the external environment.

19. The package according to claim 18 further comprising a lid coupled to the annular cover, the lid movable between: (1) a closed position in which the dispensing opening is sealed; and (2) an open position in which one of the oral care implements can pass through the dispensing opening.

20. The package according to claim 18 wherein the annular cover can be selectively rotated relative to the subcavities so that oral care implements from different subcavities can be dispensed via the dispensing opening.

21. The package according to claim 18 further comprising, for each subcavity, a transverse plate separating the subcavity into an upper chamber and a lower chamber the transverse plate having at least one opening that forms a passageway from the upper chamber to the lower chamber.

22. The package according to claim 21 further comprising a desiccant located in the lower chamber and the oral care implement located within the upper chamber.

* * * * *